(12) United States Patent
Allen et al.

(10) Patent No.: US 8,454,551 B2
(45) Date of Patent: Jun. 4, 2013

(54) REMOVABLE ADAPTER FOR PHACOEMULSIFICATION HANDPIECE HAVING IRRIGATION AND ASPIRATION FLUID PATHS

(75) Inventors: Blake Allen, Murray, UT (US); Frank A. Crandall, Salt Lake City, UT (US); Joseph Luis, West Valley City, UT (US); Olga Jovic, Midvale, UT (US); Mark Stringham, Salt Lake City, UT (US)

(73) Assignee: Zevex, Inc., Salt Lake City, UT (US)

( * ) Notice: Subject to any disclaimer, the term of this patent is extended or adjusted under 35 U.S.C. 154(b) by 957 days.

(21) Appl. No.: 12/545,457

(22) Filed: Aug. 21, 2009

(65) Prior Publication Data

US 2010/0056986 A1 Mar. 4, 2010

Related U.S. Application Data

(60) Provisional application No. 61/091,270, filed on Aug. 22, 2008.

(51) Int. Cl.
*A61B 17/20* (2006.01)

(52) U.S. Cl.
USPC .......................................................... 604/22

(58) Field of Classification Search
USPC .................... 604/20–22, 19; 606/167, 107
See application file for complete search history.

(56) References Cited

U.S. PATENT DOCUMENTS

| | | |
|---|---|---|
| 4,316,465 A | 2/1982 | Dotson |
| 4,577,629 A | 3/1986 | Martinez |
| 4,753,234 A | 6/1988 | Martinez |
| 4,804,364 A | 2/1989 | Dieras |
| 4,861,332 A | 8/1989 | Parsi |
| 4,897,079 A | 1/1990 | Zaleski et al. |
| 4,931,047 A | 6/1990 | Broadwin et al. |
| 4,979,952 A | 12/1990 | Kubota et al. |
| 4,983,901 A | 1/1991 | Lehmer |
| 5,011,471 A | 4/1991 | Miyazaki et al. |
| 5,015,227 A | 5/1991 | Broadwin |
| 5,026,387 A | 6/1991 | Thomas |
| 5,037,386 A | 8/1991 | Marcus et al. |
| 5,098,387 A | 3/1992 | Wiest et al. |
| 5,112,300 A | 5/1992 | Ureche |
| 5,123,903 A | 6/1992 | Quaid et al. |

(Continued)

FOREIGN PATENT DOCUMENTS

| | | |
|---|---|---|
| EP | 1 704 839 | 9/2006 |
| SU | 1388002 | 4/1984 |

(Continued)

OTHER PUBLICATIONS

Written Opinion of the International Searching Authority and International Search Report, Jan. 21, 2010, by Dong Won Lee.

*Primary Examiner* — Kevin C Sirmons
*Assistant Examiner* — Imani Hayman
(74) *Attorney, Agent, or Firm* — Hodgson Russ LLP (57) ABSTRACT

Current phacoemulsification handpieces require rigorous cleaning after each procedure because the aspiration and irrigation pathways for fluids are integral to the handpiece. According to the present invention, a removable horn extension and nosecone may be used with a phacoemulsification handpiece to allow for disposable fluid pathways exterior to the handpiece. This will reduce the cleaning time and effort, reduce cross-contamination, and increase the lifespan of the handpiece. Furthermore, the current invention allows different horn extensions to be used to excite different motions at the tip of the handpiece, depending on the preference of the surgeon.

19 Claims, 9 Drawing Sheets

U.S. PATENT DOCUMENTS

| | | | |
|---|---|---|---|
| 5,160,317 A | 11/1992 | Costin | |
| 5,178,605 A | 1/1993 | Imonti | |
| 5,180,363 A | 1/1993 | Idemoto et al. | |
| 5,190,517 A | 3/1993 | Zieve et al. | |
| 5,261,883 A | 11/1993 | Hood et al. | |
| 5,268,624 A | 12/1993 | Zanger | |
| 5,413,556 A | 5/1995 | Whittingham | |
| 5,453,087 A | 9/1995 | Malinowski | |
| 5,554,894 A | 9/1996 | Sepielli | |
| 5,728,130 A | 3/1998 | Ishikawa et al. | |
| 5,843,109 A | 12/1998 | Mehta et al. | |
| 5,983,749 A | 11/1999 | Holtorf | |
| 6,150,623 A | 11/2000 | Chen | |
| 6,179,829 B1 | 1/2001 | Bisch | |
| 6,251,113 B1 | 6/2001 | Appelbaum et al. | |
| 6,260,434 B1 | 7/2001 | Holtorf | |
| 6,360,630 B2 | 3/2002 | Holtorf | |
| 6,452,123 B1 | 9/2002 | Chen | |
| 6,478,766 B1 | 11/2002 | Chon | |
| 6,602,193 B2 | 8/2003 | Chon | |
| 6,674,030 B2 | 1/2004 | Chen et al. | |
| 6,740,058 B2 | 5/2004 | Lal et al. | |
| 6,852,092 B2 | 2/2005 | Kadziauskas et al. | |
| 7,012,203 B2 | 3/2006 | Hanson et al. | |
| 7,169,123 B2 | 1/2007 | Kadziauskas et al. | |
| 7,470,277 B2 | 12/2008 | Finlay et al. | |
| 2002/0138080 A1 | 9/2002 | Chon | |
| 2002/0161326 A1 | 10/2002 | Sussman et al. | |
| 2003/0073980 A1 | 4/2003 | Finlay et al. | |
| 2004/0019318 A1 | 1/2004 | Wilson et al. | |
| 2004/0024412 A1 | 2/2004 | Clements et al. | |
| 2004/0092922 A1 | 5/2004 | Kadziauskas et al. | |
| 2005/0228423 A1 | 10/2005 | Khashayar et al. | |
| 2005/0228424 A1 | 10/2005 | Khashayar et al. | |
| 2006/0036180 A1 | 2/2006 | Boukhny et al. | |
| 2006/0145540 A1 | 7/2006 | Mezhinsky | |
| 2006/0219049 A1 | 10/2006 | Horvath et al. | |
| 2008/0281253 A1 | 11/2008 | Injev et al. | |
| 2008/0294087 A1 | 11/2008 | Steen et al. | |
| 2009/0005712 A1 | 1/2009 | Raney | |
| 2010/0069825 A1 | 3/2010 | Raney | |
| 2010/0069828 A1 | 3/2010 | Steen et al. | |

FOREIGN PATENT DOCUMENTS

| | | |
|---|---|---|
| WO | WO 2008060859 | 5/2008 |
| WO | WO 2008/147771 | 12/2008 |
| WO | WO 2010/014937 | 2/2010 |
| WO | WO 2010/014942 | 2/2010 |

REMOVABLE ADAPTER FOR PHACOEMULSIFICATION HANDPIECE HAVING IRRIGATION AND ASPIRATION FLUID PATHS

PRIORITY

The present application claims the benefit of U.S. Provisional Application Ser. No. 61/091,270, filed Aug. 22, 2008, which is herein incorporated by reference in its entirety.

THE FIELD OF THE INVENTION

The present invention relates to a handpiece used to perform phacoemulsification on patients with cataracts. More specifically, the present invention relates to a handpiece with a removable horn extension and/or nosecone which function as a manifold for irrigation and aspiration fluid paths.

BACKGROUND

Phacoemulsification is a technique that has revolutionized modern eye cataract surgery. Using phacoemulsification, surgeons can remove cataracts by making only a small incision into the eye. The small incision renders sutures unnecessary and eliminates the need for general anesthesia. Most patients recover very quickly with little impairment or inconvenience.

Phacoemulsification devices work by using a handpiece with a needle at the tip that vibrates at an ultrasonic frequency to break apart and emulsify the cataract. This is typically done by selectively powering a plurality of piezoelectric elements disposed adjacent a horn (also known as a wave guide). Expansion and contraction of the piezoelectric elements causes the horn to vibrate, thus causing a needle at the end of the horn to vibrate.

A phacoemulsification handpiece essentially performs three tasks simultaneously. The tip of the needle vibrates at an ultrasonic frequency to break apart and emulsify the cataract. A saline solution is fed into the eye to irrigate and to keep the eye from collapsing, and an aspiration line removes liquid and emulsified pieces of the cataract. This maintains the anterior chamber of the eye and also cools the handpiece.

Phacoemulsification handpieces have been known since the 1960s. For example, U.S. Pat. No. 3,589,363 was obtained by Charles Kelman. Since then, many improvements have been made upon the initial device. Common current phacoemulsification handpieces consist of a an outer shell which is used as a handle, a needle which is used to break up the cataract, a horn and piezoelectric elements which are used to drive the needle and are held inside the outer shell and a plurality of fluid paths, one for aspiration and the other for irrigation. Examples of such phacoemulsification handpieces are disclosed in U.S. Pat. Nos. 5,178,605 and 5,453,087.

As with virtually any non-disposable medical device, contamination and sterilization issues are present. Because the fluid pathways are integral to the handpiece, the handpiece is contaminated with biological waste with each use. Thus, the entire handpiece must be cleaned carefully after each procedure to avoid any possible cross-contamination among patients. The handpiece must undergo a stringent sterilization after each phacoemulsification procedure, especially due to the increasing occurrence of difficult diseases to kill (e.g. Transmissible Spongiform Encephalopathies) and surgery complications potentially due to contaminants from surgical instruments (e.g. Toxic Anterior Segment Syndrome, TASS).

The sterilization procedure, while essential for patients' health, can lead to a reduction in the life of the handpiece because of the heat exposure and the difficulty in sealing the handpiece against the high temperature steam used in sterilizing. Because the handpieces are relatively expensive, reduced handpiece life can increase the cost of treating the cataract. Furthermore, the sterilization procedure takes a great deal of effort and time, and is not completely error-free. For example, TASS could be caused by cataract and lens debris which remains in the handpiece, even if the handpiece was sterilized. This may occur since the sterilization procedure relies primarily on heat and may not adequately flush the handpiece or may not flush the handpiece at all.

It would be advantageous to provide a phacoemulsification system which did not require complete sterilization of the handpiece as previously done. Thus, it is desired to provide a phacoemulsification handpiece with removable, disposable or limited use fluid pathways for potentially contaminated fluids. These connections could be disposed of after each procedure, thus reducing cleaning effort and time, reducing the risk of possible cross-contamination. Such a handpiece would benefit from an increased lifespan, since the frequency of sterilization of the handpiece could be reduced and the sterilization procedure is harmful to the handpiece.

In additional to the above, one common concern with phacoemulsification handpieces is they have traditionally provided only longitudinal motion at the tip of the needle. In some procedures it would be desirable to have a handpiece that provides lateral motion as well.

Current phacoemulsification handpieces utilize different motions to emulsify the cataract. For example, a transverse motion of the needle may be used to emulsify the cataract and overcome some of the disadvantages of the traditional longitudinal motion. However, many surgeons prefer one type of motion over the other. Furthermore, phacoemulsification handpieces are expensive and several surgeons often share the same handpiece to save on costs. Thus it is desired to provide a removable horn that allows for different tips with the same handpiece. This would allow multiple surgeons to share the same handpiece, and each could use their preferred tips. This is much more cost-effective than purchasing entire separate handpieces for each surgeon.

SUMMARY OF THE INVENTION

It is an object of the present invention to provide an improved removable horn extension and nosecone with irrigation and aspiration pathways for a phacoemulsification handpiece. It is a further object of the invention to provide a removable horn extension which allows a user to select the type of motion which is imparted to the needle.

According to one aspect of the invention, a horn extension is provided that can be easily attached to and detached from a phacoemulsification handpiece. The horn extension can be designed to excite longitudinal motion or lateral motion at the tip of the needle. The horn extension includes seals to prevent cross-contamination of fluids and reduce damping of the oscillating body.

According to another aspect of the invention, a removable nosecone is provided which can be easily attached to standard phacoemulsification handpieces. The removable nosecone includes an aspiration port which is connectable to an aspiration line independent of the remainder of the handpiece. Thus, when a procedure is finished, the nosecone and aspiration line can be removed from the remainder of the handpiece without risk that the biological contaminants in the nosecone/aspiration line will make contact with the remainder of the handpiece. This, in turn, significantly reduces the risk of contamination to other patients and lessens the amount of sterilization necessary on the handpiece.

According to another aspect of the invention, the nosecone has at least two fluid connection ports—one for aspiration and one for irrigation—but may be designed to have more fluid ports, such as a cooling port. Disposable fluid tubes are attached to the ports such that the fluid pathways enter and exit the nosecone and so that biologically contaminated fluid does not flow through the body of the phacoemulsification handpiece.

These and other aspects of the present invention are realized in a removable horn extension and nosecone for a phacoemulsification handpiece as shown and described in the following figures and related description.

BRIEF DESCRIPTION OF THE DRAWINGS

Various embodiments of the present invention are shown and described in reference to the numbered drawings wherein.

It will be appreciated that the drawings are illustrative of aspects of the present invention and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
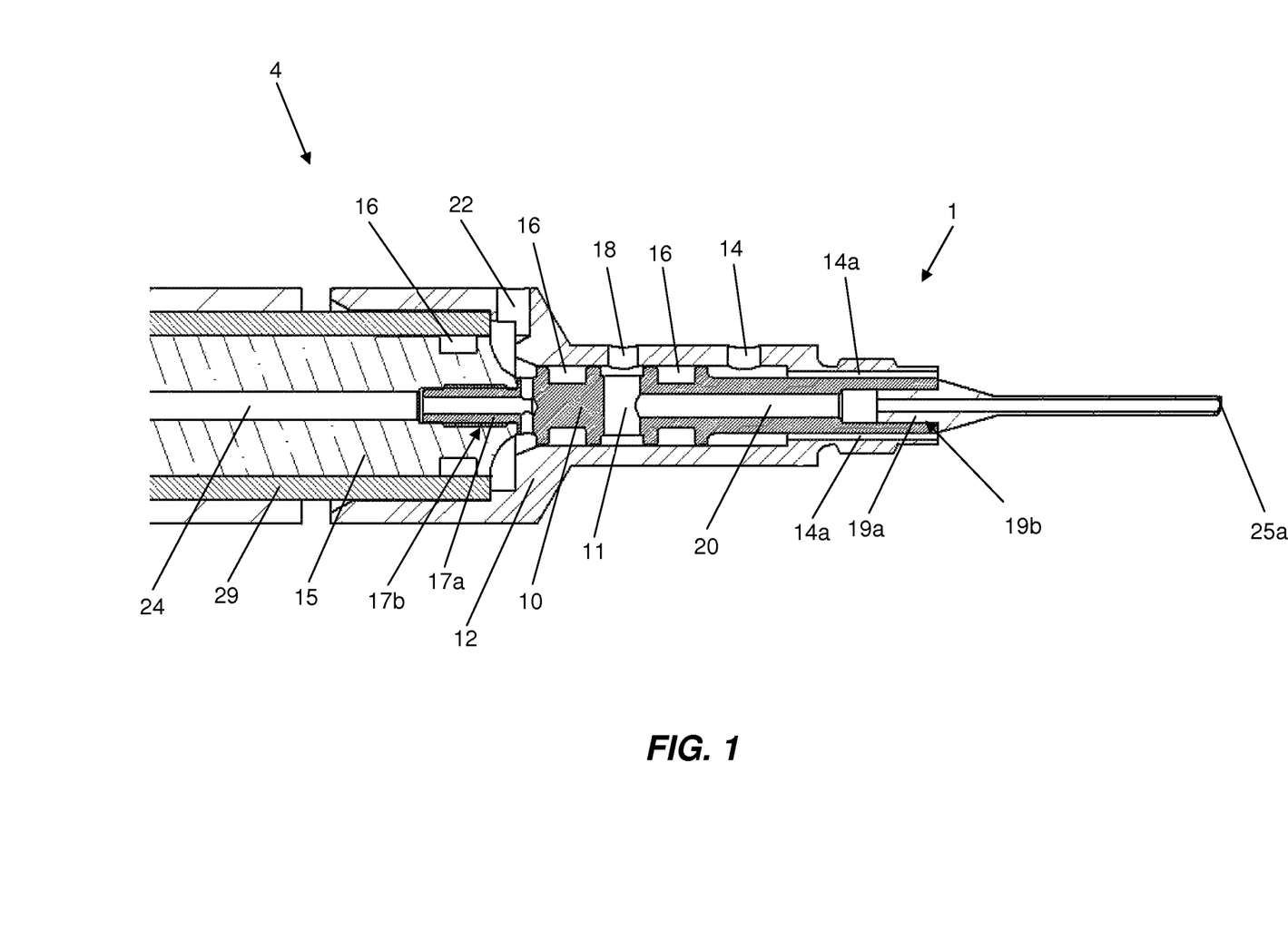
FIG. 1 shows a cross-sectional view of a removable horn extension and nosecone according to the present invention.

Turning now to FIG. 1, a cross-sectional view of a removable phacoemulsification needle adapter 1 is shown. The needle adapter 1 includes a horn extension 10 and nosecone 12. The horn extension 10 and nosecone 12 are attached to a standard phacoemulsification handpiece, generally indicated at 4. Where prior art phacoemulsification handpieces attached directly to a phacoemulsification needle, the needle adapter 1 is inserted into the handpiece 4 in place of a needle 25 and the needle 25 is attached to the needle adapter 1. Primarily, the needle adapter 1 isolates the aspirated fluids from the phacoemulsification handpiece 4 and thus alleviates the sterilization requirements for the handpiece itself, allowing the handpiece to be used for multiple procedures without a complete and rigorous sterilization procedure. The adapter 1 also allows for variation of the vibrational mode of the needle 25 while using the same handpiece 4.

The removable horn extension 10 is typically attached to the horn 15 of the surgical handpiece 4 by threaded engagement or a locking bayonet mechanism, exemplified by threaded projection 17a and a threaded socket 17b. The horn 15 is also known as a wave guide, and is driven by a plurality of piezoelectric elements (not shown) forming a Langevin-style transducer. Ordinarily, the horn 15 would have threads or some other mechanism such as the threaded socket 17b for attachment to a standard phacoemulsification needle 25. This mechanism would be used to attach the horn extension 10, and the horn extension would typically include a similar attachment mechanism such as a threaded socket 19b which receives the threads 19a on the needle 25.

Wrench flats may be disposed on one or more of the horn extension 10 and horn 15 for ease in connecting the horn extension to the handpiece 4 and needle 25. Thus, the horn extension 10 is mounted on the horn 15 where the needle would typically be attached in a prior art configuration, and the needle 25 is attached to the horn extension. Alternatively, the needle may be integrally formed with the horn extension.

Seals 16 are positioned around a 90 degree bend (bore 11 through the horn extension) in the fluid path (lumen 20) connecting an aspiration port 18 to the center aspiration lumen 20 of the horn extension 10. These seals 16 prevent cross-contamination or fluid leakage. In use, the emulsified cataract and liquid from the eye are drawn in through the needle tip 25a, down the needle 25, through the center lumen 20, and out the aspiration port 18.

The horn extension 10 is covered by a nosecone 12. As shown, the nosecone 12 has a plurality of fluid connection ports 14, 18, 22. The fluid connection ports include a port for aspiration 18 and may include a port for irrigation 14. As shown in FIG. 1, the nosecone 12 includes three fluid connection ports: an aspiration port 18, an irrigation port 14, and a cooling fluid port 22. Irrigation solution flows through the irrigation port 14 and through an irrigation passage 14a during a surgical procedure. The cooling fluid port 22 may have access to one or more lumens (such as the center lumen 24) in the horn 15. The cooling fluid cools the piezoelectric elements and adjacent structures of the handpiece 4 and prolongs the life of the handpiece as well as increasing the comfort in using the handpiece. It will be appreciated that cooling the handpiece stack may be achieved by other means as will be described below.

The phacoemulsification handpiece includes a sleeve or outer shell 29 which surrounds the horn 15 and forms the outer surface of the handpiece 4. The outer shell 29 is held by the user when using the handpiece. The nosecone 12 is typically attached to the handpiece outer shell 29. The nosecone 12 may be attached to the ultrasonic handpiece by threads, a bayonet style locking mechanism, or other suitable means. The nosecone 12 may also be held in place via the threads 17a which hold the horn extension 10 to the horn 15.

Figure 2:
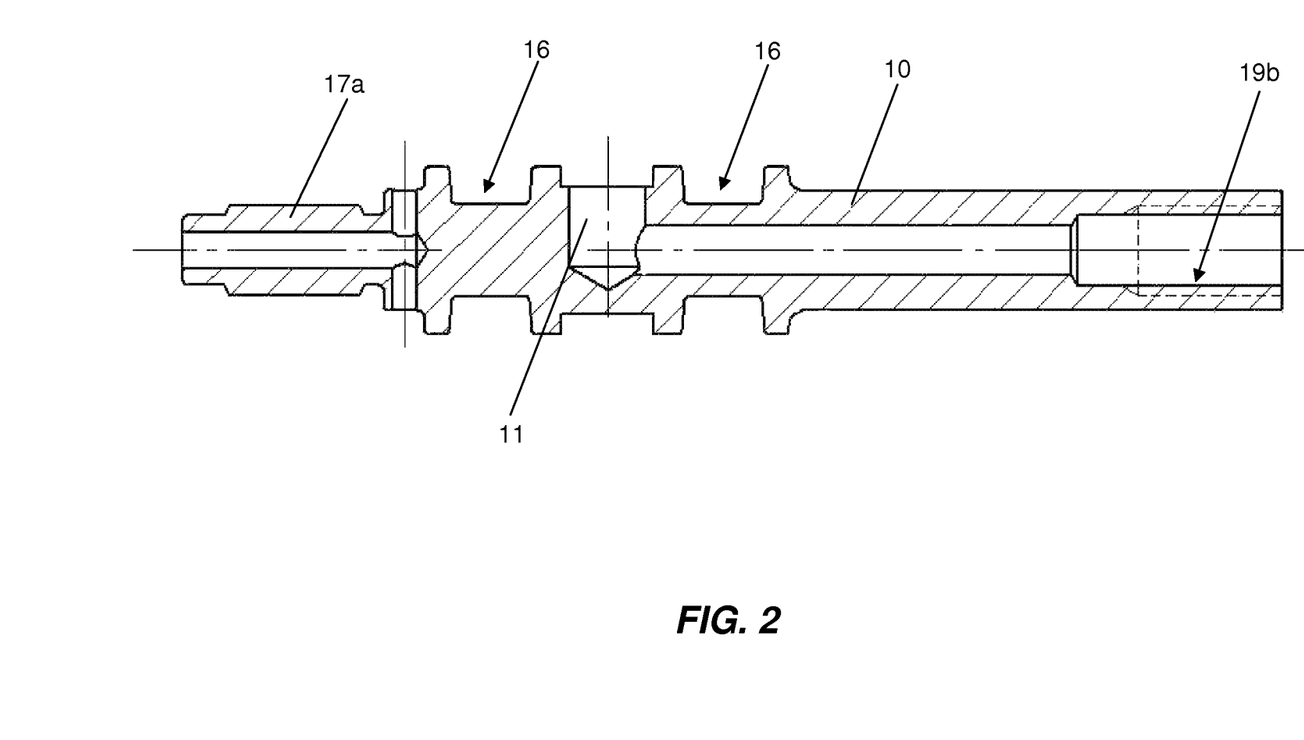
FIG. 2 shows a cross-sectional view of the removable horn extension of FIG. 1 having a configuration designed to cause lateral needle motion.

Turning now to FIG. 2, a cross-sectional view of a horn extension 10 that excites lateral motion of the needle 25 according to the present invention is shown. Surgeons may prefer different types of motion (longitudinal versus lateral motion of the needle) according to the particular surgery being performed or according to the tendencies of the individual surgeon. Additionally, multiple surgeons in a group practice may use the same common handpiece 4 to reduce the operational cost associated with their medical practice. According to the present invention, they may switch the adapter 1 to use a different horn extension 10 in order to achieve the desired motion. The horn extension 10 shown in FIG. 1 produces longitudinal vibration of the needle 25 because the horn extension is symmetrical about its central axis. The horn extension 10 also produces lateral vibration of the needle tip (flexing of the needle) because the horn extension is not symmetrical about its central axis. The horn extension 10a utilizes an asymmetric hole 11 through the horn extension body.

The particular horn extension 10 is constructed so that the lateral bore 11 of the aspiration port extends from one side of the horn extension to the center of the horn extension rather than extending completely through the horn extension 10 as shown by the lateral bore 11 in FIG. 1. Asymmetry may be used to produce lateral motion of the needle tip 25a. The present invention thus provides a simple and convenient way of producing either longitudinal vibration or lateral vibration as is desired from a single phacoemulsification handpiece 4. Surgeons may thus have greater control over the surgical procedure without the cost of having two handpieces 4.

Figure 3:
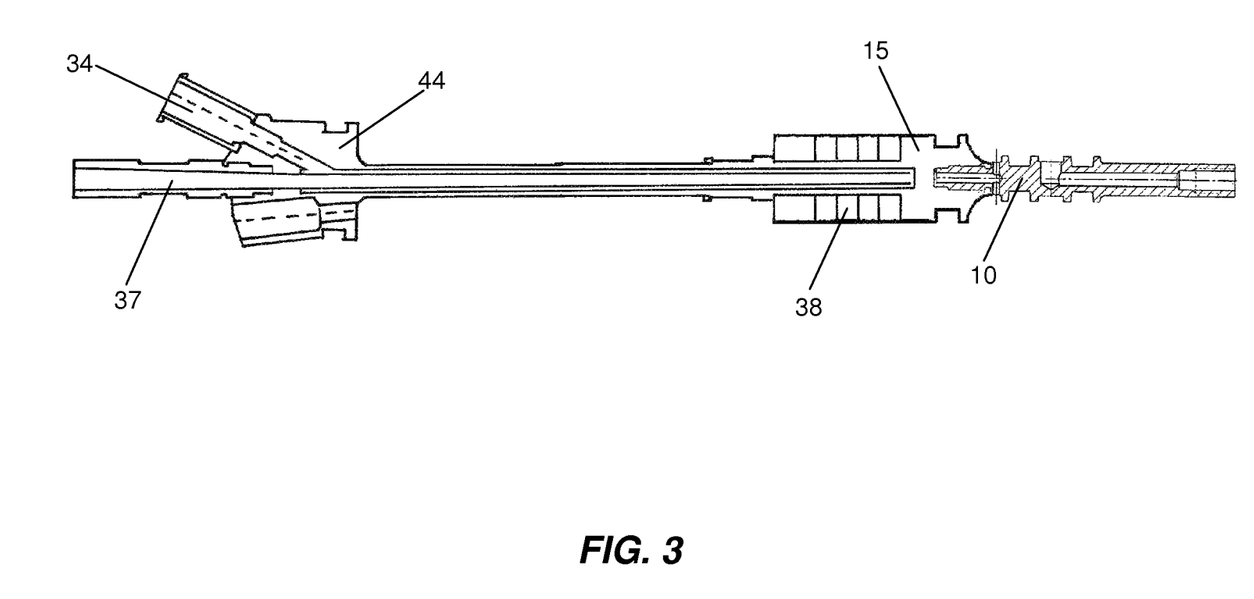
FIG. 3 shows a cross-sectional view of a the interior components of a standard phacoemulsification handpiece with the horn extension of FIG. 1.

FIG. 3 shows a cross-sectional view of the horn extension 10 according to the current invention attached to the horn 15 of a standard ultrasonic handpiece 4 with the outer shell of the handpiece and the nosecone of the horn extension omitted. Another method for cooling the handpiece stack, rather than a third fluid connection site at the nosecone, is through connections in the rearsection 44 of the handpiece 4. Cooling fluid may be circulated through the handpiece stack by providing a coolant supply 34 and a coolant return 37. The piezoelectric elements 38 convert electrical energy into mechanical energy to oscillate the horn 15, and thus produce heat. The cooling fluid removes heat generated by the mechanical movement of the piezoelectric elements 38 and horn 15.

Figure 4:
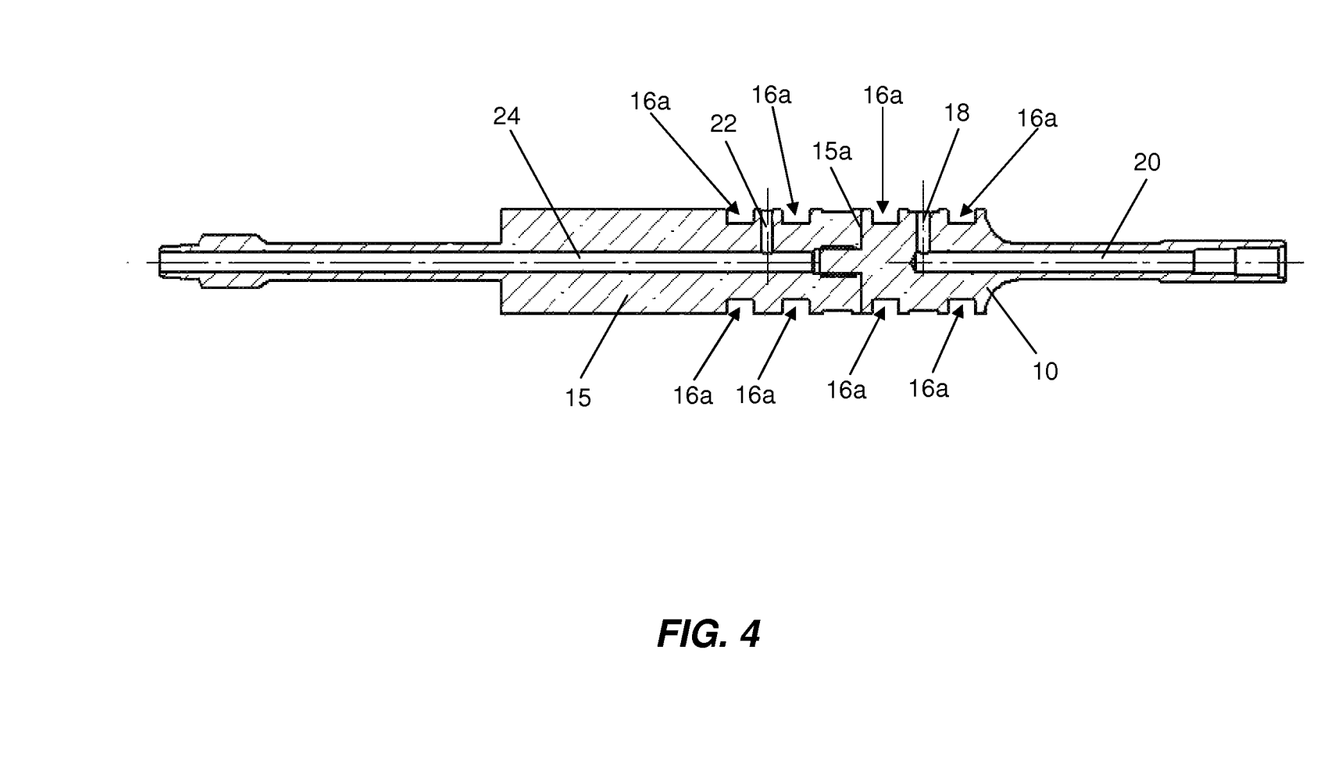
FIG. 4 shows a cross-sectional view of an alternative handpiece of the present invention designed with the aspiration lumen and seal grooves incorporated on the large diameter of the horn.

Turning now to FIG. 4, an improved handpiece design of the present invention is shown. The horn 15 includes a front face 15a which is larger in diameter and which provides a larger mating area for contacting the horn extension 10. An aspiration port 18 is provided in fluid communication with a central aspiration lumen 20 of the horn extension 10. Seal grooves 16a are formed on the large diameter of the horn extension 10. Similar seal grooves 16a are formed in the horn 15 in order to seal around a cooling fluid port 22 which passes cooling fluid through horn 15 and handpiece via a cooling lumen 24. Seals are placed in the seal grooves 16a as shown previously. The use of a horn 15 with a larger diameter front face 15a mated to the larger end of a horn extension 10 provides for less motion at the large diameter of the horn 15 and horn extension 10. This reduces motion around the seal grooves 16a and results in less heating and acoustic losses.

Figure 5:
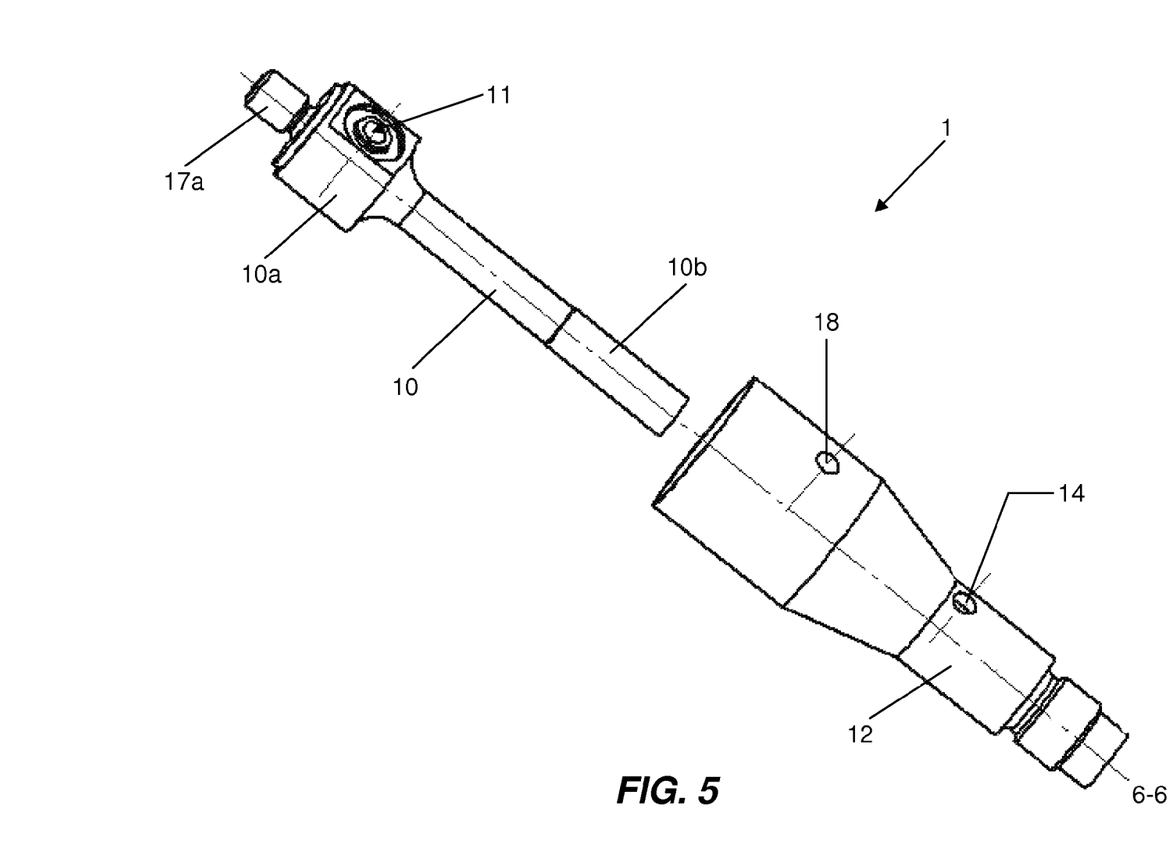
FIG. 5 shows a perspective view of the nosecone and horn extension of the current invention joined in one assembly.

FIG. 5 shows another exploded perspective view of a phacoemulsification needle adapter 1 of the present invention. The nosecone 12 and horn extension 10 are combined into one assembly which eliminates some of the seals between the horn extension and nosecone. The nosecone 12 and horn extension 10 form a unitary adaptor 1 which connects to both an ultrasonic handpiece 4 and a needle 25. The adaptor 1 can be molded together such as by molding the nosecone 12 around the horn extension 10, or can be made by attaching the horn extension 10 to the nosecone 12 by bonding, sealing or otherwise attaching various components. It is preferred, though not required, that the bonding or sealing occurs at a step in the horn extension (such as at the larger diameter base 10a of the horn extension) where a vibrational node having minimal motion occurs so as to reduce losses. An irrigation port and 14 and aspiration port 18 are formed in the nosecone 12. The irrigation port 14 would be connected to irrigation passages 14a (not shown) to allow irrigation fluid to pass out the tip of the adapter 1. A threaded extension 17a or other suitable attachment means is provided at the base end 10a of the assembly for attachment to the horn of a standard phacoemulsification handpiece as has been shown.

The adaptor assembly 1 (including the various horn extensions and nosecones shown in FIGS. 1 through 9) provides a convenient method for allowing phacoemulsification handpieces to be used repeatedly without requiring complete sterilization between each use, and for allowing a handpiece to be used with different tips and vibrational modes. The adaptor assembly 1 allows the aspirated biological material to be drawn out of the aspiration port 18 so that the biological material never comes into contact with the handpiece. Similarly, the irrigation port 14 allows irrigation fluid to pass only through the adaptor 1 and not through the handpiece. When the procedure is finished, the adaptor assembly 1 can be removed and sterilized or simply discarded. As such the handpiece and its piezoelectric elements need not be subject to rigorous sterilization procedures since the handpiece is not contacted with the biological material or fluids which are introduced into the patient. The handpiece may simply be decontaminated to clean the exterior of the handpiece. Eliminating or reducing the frequency at which the handpiece is rigorously sterilized is anticipated to lengthen its useful life, as the sterilization procedures are harmful to the handpiece piezoelectric elements.

As the adaptor assembly 1 has no piezoelectric elements, it is relatively inexpensive to manufacture (allowing it to be disposable if necessary) and allowing the adapter to be sterilized using conventional processes without significant risk that the sterilizing process will damage the adaptor assembly. This also allows a handpiece to be used for multiple surgeries without complete sterilization therebetween by using a different adapter for each surgery. The adapters may be disposed of or sterilized between uses as is desired. As surgical equipment is often sterilized after the day has ended, prior art handpieces often required that a surgeon had a separate handpiece for each surgery which was to be performed during the day, and all of the handpieces were sterilized after the end of the day. The cost of the handpieces is burdensome and may prevent a surgeon from performing a higher number of surgeries during a day. The present invention allows a surgeon to perform multiple surgeries in a single day with a single handpiece, rather than requiring a separate handpiece by simply requiring the surgeon to have multiple adapter assemblies 1 (with the horn extension and nosecone) which may be sterilized or disposed of after the procedures. The present invention thus allows a greater number of persons to be treated while reducing the cost to treat each person.

Figure 6:
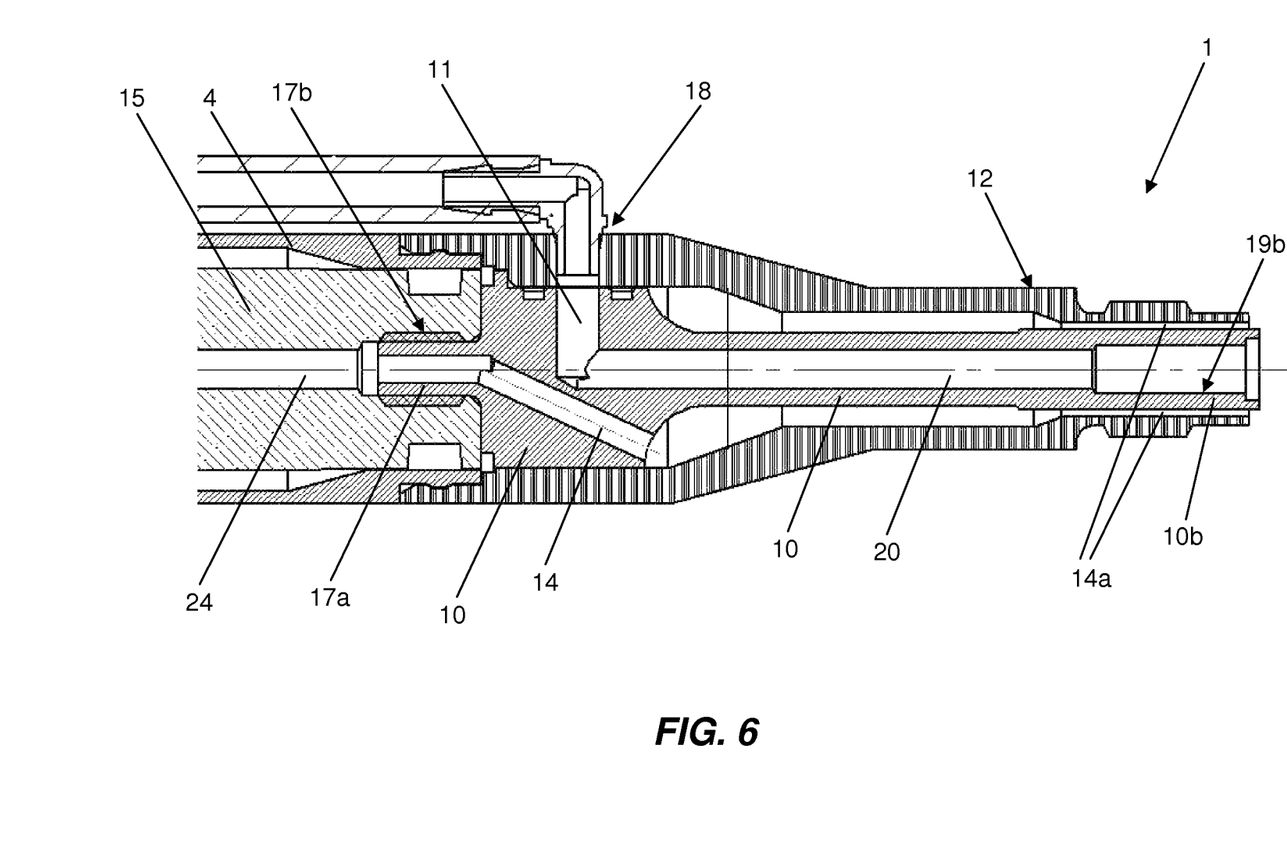
FIG. 6 shows a cross-sectional view of the nosecone and horn extension of FIG. 5.

FIG. 6 shows a cross-sectional view of the adaptor assembly 1 of FIG. 5 taken along the line 6-6. The shape of the horn extension 10 and the nosecone portion 12 of the adapter 1 are visible, showing how the horn extension and the nosecone are connected together at the base 10a of the horn extension 10. It can be seen how the aspiration port 18 is in fluid communication with a central aspiration lumen 20 to draw fluid and biological material through the lumen. A seal 16 may be provided between the horn extension 10 and the nosecone 12 to ensure a good seal of the aspiration lumen between the horn extension 10 and the nosecone 12. FIG. 6 illustrates how the irrigation port 14 may be fluidly connected to the lumen 24 of the handpiece 4 and to one or more irrigation passages 14a disposed between the horn extension 10 and the nosecone 12, eliminating an external connection.

A threaded extension 17a or other connection such as a bayonet style locking mechanism allow for attaching to the handpiece horn 15 of a phacoemulsification handpiece. The tip 10b of the horn extension 10c is configured to receive a needle 25 as previously shown. Alternatively, the horn extension may include the needle as a part thereof, and the whole assembly may be sterilized or discarded as is appropriate. By combining the horn extension 10 and nosecone 12 into one adaptor assembly 1 assembly, an inexpensive adapter is provided which is quite easy to use with little risk or leaking or failure. Additionally, sealing occurs at a vibrational node, which is more efficient than sealing at off-nodal locations because there is less damping of the oscillating body. The adaptor assembly 1 shown is easy to use because it requires only hand tightening.

Figure 7:
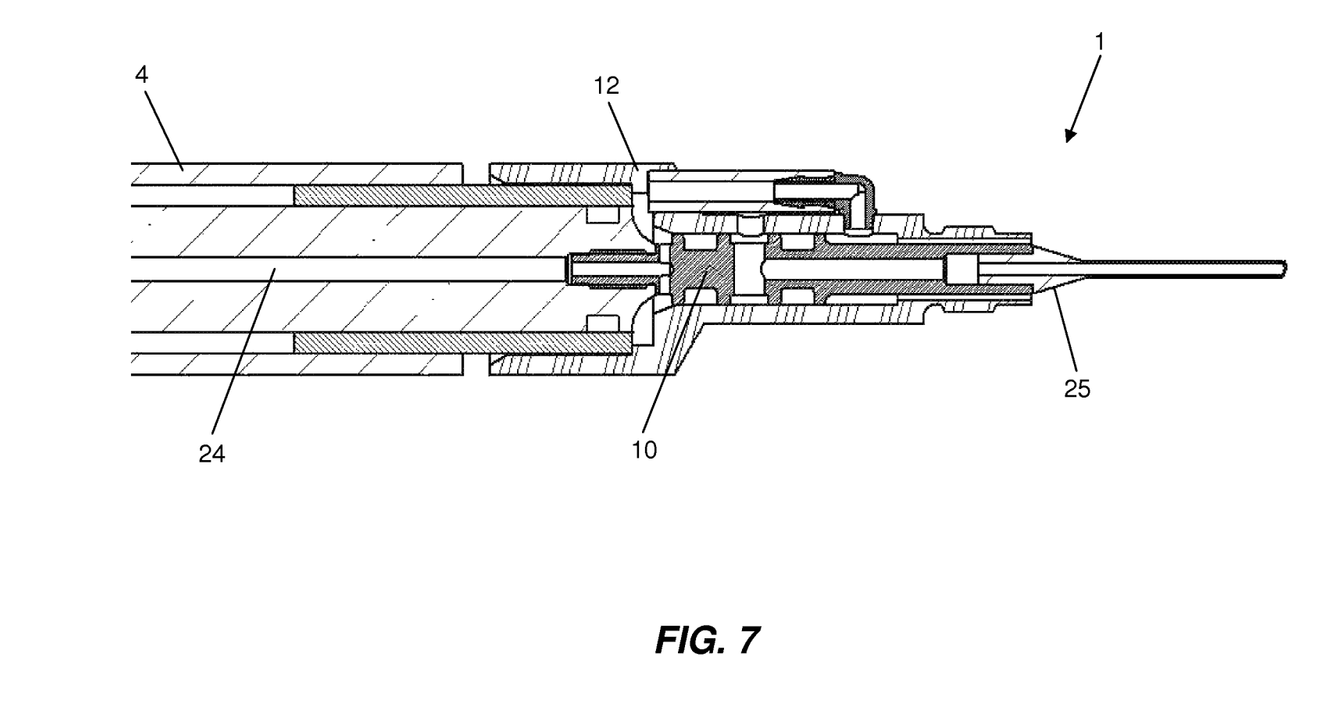
FIG. 7 shows a cross-sectional view of a standard phacoemulsification handpiece with the removable horn extension and nosecone according to the present invention attached thereto.

Turning now to FIG. 7, a cut away side view of a standard phacoemulsification handpiece 4 is shown with an adapter 1 having a removable horn extension 10 and nosecone 12 in accordance with the present invention attached. The horn extension 10 and nosecone 12 are similar to those shown in FIG. 1. A luer connection 84 and clean saline (irrigation) inlet 80 are disposed at the end of the handpiece. The irrigation path travels along a central lumen 24 which extends through the center of the handpiece 4. In the process, the irrigation solution passes through the piezoelectric elements 38 and cools the horn.

Figure 8:
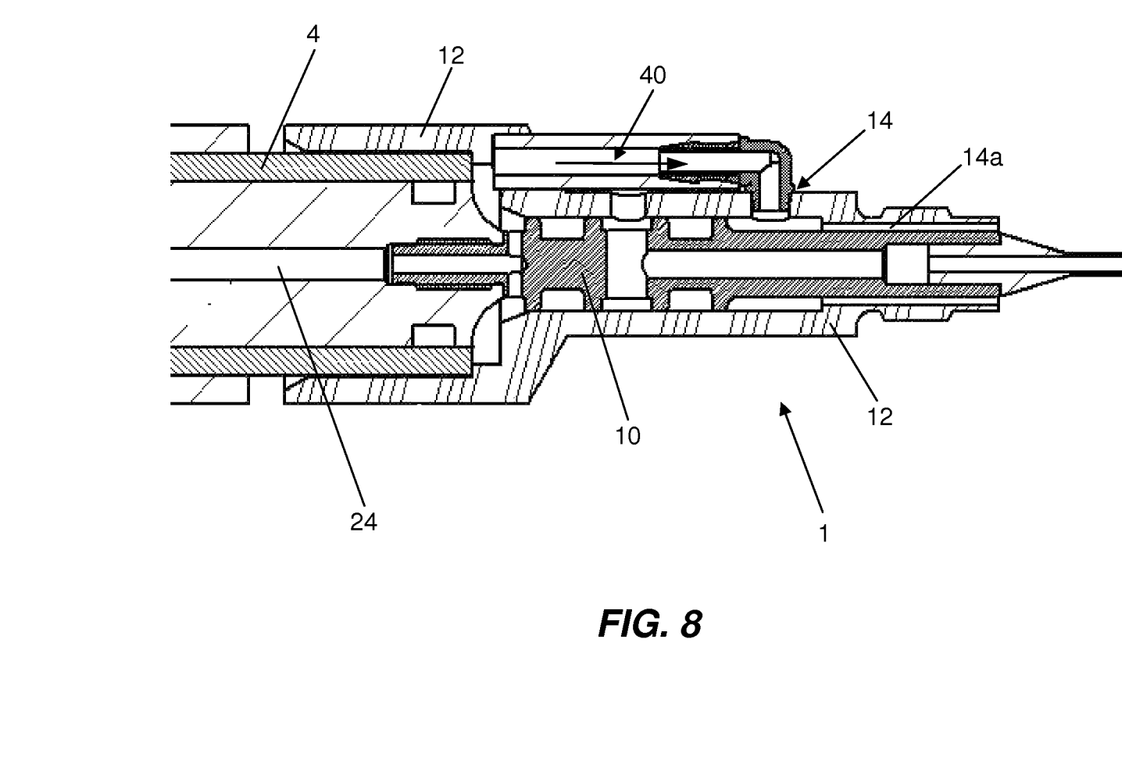
FIG. 8 shows a detailed view of the irrigation fluid pathway shown in FIG. 7 in accordance with the present invention.

FIG. 8 shows a detailed view of the path taken by the irrigation solution through the handpiece 4 and adapter 1 of FIG. 7. As the irrigation solution comes to end of the central lumen 24, the irrigation solution flows outwardly, leaving the handpiece 4 and entering an irrigation passage 40 which may be formed as part of nosecone 12 or which may be external thereto. After entering the nosecone 12, the irrigation solution continues on its flow through the irrigation passage 14a along the horn extension 10 and out adjacent the needle 25 where it irrigates the eye during surgery.

The removable horn extension 10 and nosecone 12 may be designed to be retrofitted into most phacoemulsification systems in the field. The system requirements for the piezoelectric elements handpiece 4, such as frequency and impedance, can be designed into the current invention through proper selection of material and horn extension size to thereby match the existing handpiece 4. As will be appreciated by the description of the invention, one or more of the existing fluid pathways and connections of the handpiece may be used without requiring a separate system of fluid lines. In some cases, it may be advantageous to utilize the irrigation or cooling fluid pathways of the handpiece 4, and even the aspiration pathway as well. In such a case, the present invention is advantageous as it still separates the needle 25 and adapter 1 from the handpiece 4 and thereby reduces the risk of contamination. Additionally, the adapter 1 allows the surgeon to choose between longitudinal or longitudinal and lateral vibration of the needle 25 without requiring an additional handpiece 4. According to other aspects of the invention, one or more of the fluid pathways such as the irrigation and aspiration pathways may be isolated from the handpiece 4 such that the handpiece need not undergo such a rigorous sterilization. In addition to the other advantages of the invention, this extends the life and reduces the failure risk of the handpiece 4.

Figure 9:
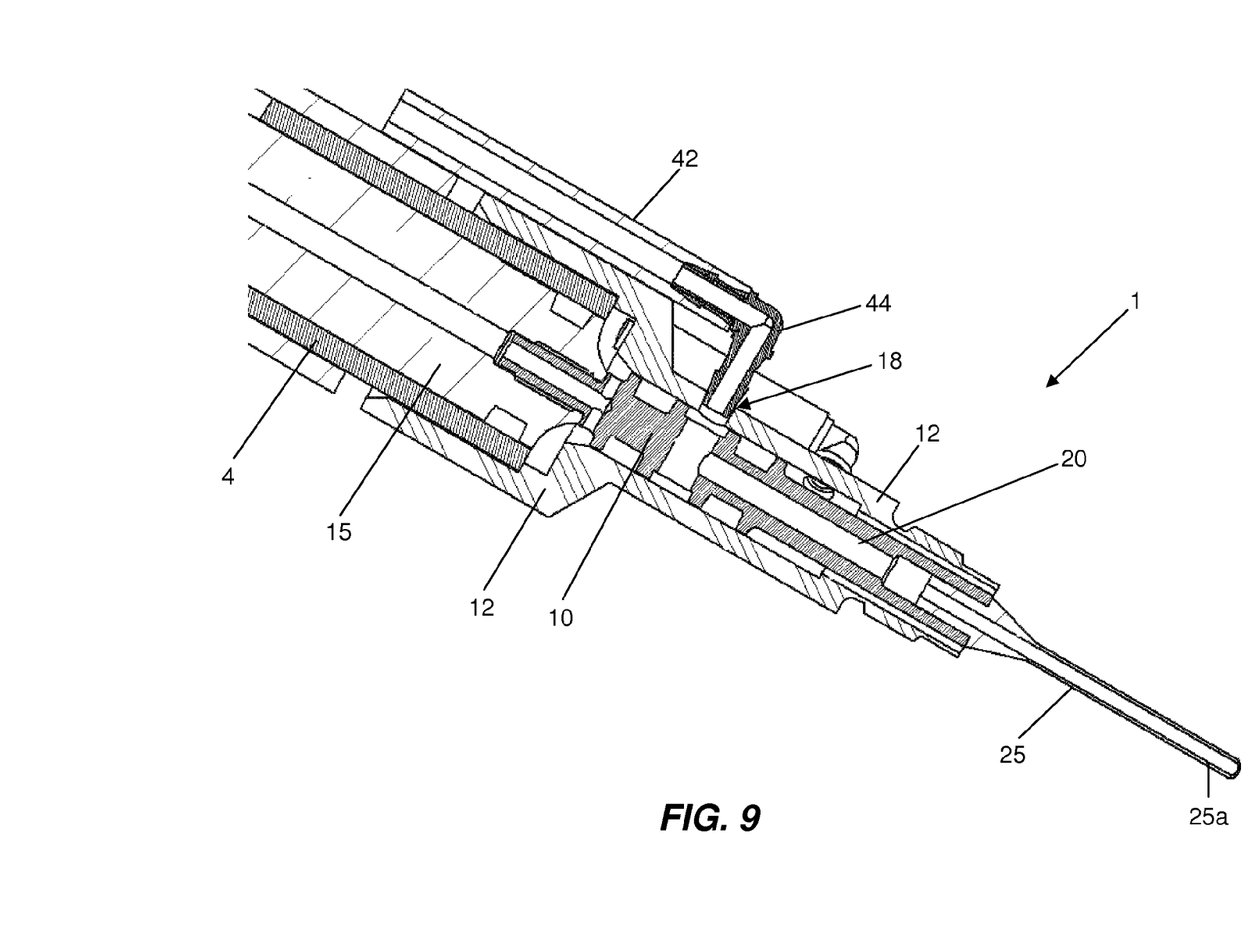
FIG. 9 shows a detailed view of the aspiration fluid pathway shows in FIG. 7.

Turning now to FIG. 9, a partially cut away side view of the handpiece and adapter of FIG. 7 is shown. The aspiration fluid pathway is discussed to facilitate an understanding thereof. Aspirated fluids, including a fluid such as saline and biological tissue from the eye are drawn into the tip 25a of the needle 25, through the needle lumen horn extension lumen 20. Aspirated fluids exit the center of the horn extension 10 through a lateral bore 11 or channel leading to the aspiration port 18 in the nosecone 12. The fluids then travel through tubing 42 which is exterior to the handpiece 4 of the phacoemulsification device.

The tubing 42 may bend at about a ninety degree angle or use a similarly shaped elbow fitting 44 so that the tubing continues adjacent to the exterior of the handpiece 4. Having the tubing 42 disposed adjacent the handpiece helps to keep the tubing from interfering with the surgeons work while operating on patients. Being disposed on the exterior of the handpiece 4, the tubing 42 can easily be removed and disposed of after each surgical procedure. The nosecone 12 and horn extension 10 may also be discarded, or they may be easily sterilized for reuse. Thus, the biological material which has been aspirated from the eye avoids contact with the handpiece 4 and the various structures which are in contact with the biological material are easily sterilized or inexpensive and disposable.

While handpiece 4 shown does come into contact with the irrigation solution, the irrigation solution is typically sterile saline. Thus, minimal sterilization procedures need be taken with the handpiece 4. This will reduce cross-contamination and cleaning time as well as extend the life of the handpiece 4.

There is thus disclosed an improved removable horn extension and nosecone for use with a phacoemulsification handpiece. It will be appreciated that numerous changes may be made to the present invention without departing from the scope of the claims.

What is claimed is:

1. A needle adapter for a phacoemulsification handpiece comprising: a horn extension, the horn extension having a first end configured for attachment to a phacoemulsification handpiece and a second end configured for attachment to a phacoemulsification needle; a nosecone, the nosecone extending around the horn extension; an irrigation fluid pathway disposed between the horn extension and the nosecone for providing fluid to the phacoemulsification needle; an aspiration pathway through the horn extension for receiving aspirated fluid from a lumen of the phacoemulsification needle; wherein the aspiration fluid pathway exits the horn extension and does not pass through the phacoemulsification handpiece; wherein the aspiration pathway includes a bore, which extends into a side of the horn extension and the lumen, the bore being in fluid communication with an aspiration port in the nosecone.

2. The needle adapter of claim 1, wherein the irrigation fluid pathway is configured for fluid connection to a phacoemulsification handpiece such that the handpiece provides fluid to the irrigation fluid pathway.

3. The needle adapter of claim 1, wherein the first end of the horn extension is configured for attachment to a needle receptacle of a phacoemulsification handpiece, and wherein the second end of the horn extension has a needle receptacle for receiving the phacoemulsification needle.

4. The needle adapter of claim 1, wherein the horn extension is laterally asymmetrical so as to cause lateral vibration of the phacoemulsification needle.

5. The needle adapter of claim 1, further comprising a cooling fluid connection for directing cooling fluid through the handpiece.

6. The needle adapter of claim 1, wherein the cooling fluid connection circulates cooling fluid through the handpiece.

7. A system comprising the needle adapter of claim 1, further comprising a phacoemulsification handpiece, and wherein the first end of the horn extension is attached to the handpiece horn.

8. The system of claim 7, wherein irrigation fluid travels through the handpiece, through the needle adapter, and exits adjacent the phacoemulsification needle.

9. The system of claim 7, wherein the aspirated material enters a needle tip, travels through the needle lumen, through the lumen, and exits the nosecone without entering the phacoemulsification handpiece.

10. The needle adapter of claim 1, wherein the first end of the horn extension has a threaded projection for engaging a threaded recess on a phacoemulsification handpiece, and wherein the second end of the horn projection has a threaded recess for receiving the phacoemulsification needle.

11. The needle adapter of claim 1, further comprising an external irrigation passage for transporting irrigation fluid from a phacoemulsification handpiece to an irrigation port on the nosecone and thereby deliver the irrigation fluid to the irrigation fluid pathway.

12. The needle adapter of claim 1, wherein the bore is a lateral bore disposed in alignment with the aspiration port in the nosecone.

13. A phacoemulsification system comprising: a phacoemulsification handpiece, the handpiece comprising a body, a horn, piezoelectric elements disposed on the horn, and a socket disposed on an end of the horn for receiving a phacoemulsification needle; a phacoemulsification needle adapter comprising; a horn extension, the horn extension having a projection on a first end thereof, the projection being attached to the handpiece socket, the horn having a socket on a second end thereof opposite the first end for receiving the phacoemulsification needle; a nosecone, the nosecone being disposed around the horn extension; an irrigation passage configured for receiving irrigation fluid from the handpiece and for delivering the irrigation fluid to the phacoemulsification needle; an aspiration pathway configured for receiving aspirated fluids from a phacoemulsification needle tip and for transporting said fluids through the needle adapter and out of the needle adapter without passing through the phacoemulsification handpiece; wherein the aspiration pathway includes a bore, which extends into a side of the horn extension, the bore being in fluid communication with an aspiration port in the nosecone; and wherein the phacoemulsification needle is attached to the needle adapter socket.

14. The system of claim 13, wherein the aspiration fluid pathway passes through a needle bore, through a horn extension central lumen, through the bore in the horn extension, and through the aspiration port in the nosecone.

15. The system of claim 13, wherein the irrigation passage passes from the handpiece, through the horn extension, between the horn extension and the nosecone, and adjacent the needle.

16. The system of claim 13, wherein the irrigation passage passes from the handpiece, out through the nosecone, along an external passage, through the nosecone, between the nosecone and the horn extension, and adjacent the needle.

17. The system of claim 13, wherein the end of the handpiece horn adjacent the horn extension is substantially the same diameter as the piezoelectric elements, and wherein the first end of the horn extension is substantially the same diameter as the piezoelectric elements, and wherein the second end of the horn extension is a reduced diameter.

18. A method of using a phacoemulsification handpiece comprising: selecting a phacoemulsification handpiece, the handpiece having a piezoelectric element, a horn, a body, and a horn socket for receiving a phacoemulsification needle; attaching a first end of a phacoemulsification needle adapter to the horn socket, the needle adapter comprising a horn extension and a nosecone; attaching the phacoemulsification needle to a second end of the needle adapter opposite the first end; and operating the handpiece such that irrigation fluid flows through the handpiece, through the needle adapter, and adjacent the needle and such that aspirated fluid flows through the needle, through the needle adapter, and out of the needle adapter such that the aspirated fluid does not contact the handpiece.

19. The method of claim 18, wherein the method comprises selecting a needle adapter having an asymmetrical bore through a side thereof so as to introduce lateral vibration to the phacoemulsification needle tip.

\* \* \* \* \*